(12) United States Patent
Ozaki et al.

(10) Patent No.: US 6,743,944 B1
(45) Date of Patent: Jun. 1, 2004

(54) PROCESS FOR PRODUCING OPTICALLY ACTIVE AMINOALCOHOL

(75) Inventors: Eiji Ozaki, Hiroshima (JP); Takakazu Endou, Yokohama (JP); Yasumasa Yamaguchi, Yokohama (JP); Mitsuharu Hamanaka, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 113 days.

(21) Appl. No.: 10/070,365

(22) PCT Filed: Sep. 7, 2000

(86) PCT No.: PCT/JP00/06092

§ 371 (c)(1),
(2), (4) Date: Mar. 6, 2002

(87) PCT Pub. No.: WO01/17944

PCT Pub. Date: Mar. 15, 2001

(30) Foreign Application Priority Data

Sep. 7, 1999 (JP) .............................. 11-252902
Jul. 6, 2000 (JP) ....................... 2000-205074

(51) Int. Cl.[7] .............................................. C07C 59/48
(52) U.S. Cl. ..................................... 562/470; 562/401
(58) Field of Search ................................. 562/470, 401

(56) References Cited

U.S. PATENT DOCUMENTS

| | | | |
|---|---|---|---|
| 3,553,257 A | 1/1971 | Halmos et al. | |
| 4,239,912 A | 12/1980 | Halmos | |
| 4,259,521 A | * 3/1981 | Kazan et al. | ............... 562/401 |
| 4,260,815 A | 4/1981 | Kazan et al. | |
| 4,330,484 A | 5/1982 | Berning et al. | |
| 5,770,590 A | 6/1998 | Natsugari et al. | |

FOREIGN PATENT DOCUMENTS

| | | |
|---|---|---|
| EP | 000 518 | 2/1979 |
| EP | 089 139 | 9/1983 |
| JP | 54024849 | 2/1979 |
| JP | 580443939 | 2/1979 |
| JP | 4-99496 | 3/1992 |
| JP | 4-222591 | 8/1992 |
| JP | 7188124 | 7/1995 |
| JP | 8291157 | 11/1996 |

OTHER PUBLICATIONS

Corse et al., "Dihydrozeatin: an improved synthesis and resolution of both polymers," Journal of Plant Grown Regulation, VOl. 2, No. 1, 1983, pp. 47–57.

Adams et al., The Absolute Configuration of the $C_1$ Atom in Retronecanone (1–Methyl–7–oxopyrrolizidine), $C_1$ Atom in Retronecanone, vol. 81, Sep. 20, 1959, pp. 4946–4951.

* cited by examiner

Primary Examiner—Paul J. Killos
Assistant Examiner—Hector M. Reyes
(74) Attorney, Agent, or Firm—Fitch, Even, Tabin & Flannery

(57) ABSTRACT

An industrially advantageous process for producing optically active 4-amino-2-methylbutane-1-ol which is useful as an intermediate in synthesizing optically active medicines and pesticides. Racemic 4-amino-2-methylbutane-1-ol is treated with an optically active organic acid. The diastereomeric salt thus obtained is crystallized out and subjected to solid-liquid separation to give optically active 4-amino-2-methylbutane-1-ol. The diastereomeric salt of optically active 4-amino-2-methylbutane-1-ol with an optically active reagent for optical resolution is decomposed by bringing into contact with a solvent and an alkali and subjected to solid-liquid separation, thereby recovering the optically active 4-amino-2-methylbutane-1-ol from the filtrate. Further, the filtration residue containing the alkali salt of the reagent for optical resolution obtained by the solid-liquid separation is brought into contact with a solvent and an acid. Then the reagent for optical resolution thus crystallized out is subjected to solid-liquid separation and recovered.

5 Claims, 3 Drawing Sheets

PROCESS FOR PRODUCING OPTICALLY ACTIVE AMINOALCOHOL

This is a National Stage application of International Application No. PCT/JP00/06092, which was filed on Sep. 7, 2000, which designated the U.S., and was not filed in the English language.

TECHNICAL FIELD

This invention relates to a process for producing optically active 4-amino-2-methylbutane-1-ol useful as an intermediate for synthesizing optically active medicines and pesticides, a salt of optically active 4-amino-2-methylbutane-1-ol with an optically active organic acid, a process for producing the salt, a process for producing optically active 4-amino-2-methylbutane-1-ol by using the salt, a process for using the optically active 4-amino-2-methylbutane-1-ol obtained by the above-mentioned process as an intermediate for synthesizing optically active medicines and pesticides, and a process for producing optically active medicines and pesticides by using the optically active 4-amino-2-methylbutane-1-ol obtained by the above-mentioned process.

BACKGROUND ART

With regard to a process for producing optically active 4-amino-2-methylbutane-1-ol, there have been reported a process for synthesizing the compound by reducing optically active 2-methyl-4-aminobutyric acid with lithium aluminum hydride (J. Am. chem. Soc., 81, 4946–4951 (1959)) and a process for synthesizing the compound by reducing a methyl ester of optically active 2-methyl-4-nitrobutyric acid with lithium aluminum hydride (J. Plant Growth Regul. 2 (1), 47–57 (1983))

However, the former process has a disadvantage of low yield; in the latter process, the safety of nitromethane used as a starting material and the yield of its addition reaction are low, hence it is difficult to use such processes as an industrial production process.

On the other hand, as to a process for producing racemic 4-amino-2-methylbutane-1-ol, it can be prepared, for example, by obtaining methyl-3-cyanoisobutyrate from hydrocyanic acid and methyl methacrylate, and then reducing the product with an alkali metal hydride in a suitable solvent according to a process described in JP-A-8-291157. However, no report has been made about an optical resolution of racemic 4-amino-2-methylbutane-1-ol as in the present invention.

With regard to a formation of a diastereomeric salt of an optically active organic acid (optically active reagent for optical resolution) with a low molecular weight aminoalcohol, there are known a salt of optically active mandelic acid with optically active 2-amino-1-butanol (US 4260815A, US 4259521A, and EP 518B1) and a salt of said optically active mandelic acid with optically active 2-benzylamino-1-butanol (US 4239912A). However, these amino-alcohols referred to in these documents are restricted only to β-amino-alcohols in which an amino group is directly bonded to asymmetric carbon and it has been utterly unknown whether or not these disclosures can be applied to 4-amino-2-methylbutane-1-ol of this invention, that is, a compound in which the amino group is not directly bonded to asymmetric carbon, or not.

DISCLOSURE OF THE INVENTION

The object of this invention is to provide an industrially advantageous process for producing optically active 4-amino-2-methylbutane-1-ol useful as an intermediate for synthesizing optically active medicines and pesticides.

The other objects of this invention are to provide a process for producing, industrially advantageously, optically active 4-amino-2-methylbutane-1-ol from a diastereomeric salt of optically active 4-amino-2-methylbutane-1-ol with an optically active reagent for optical resolution and a process for recovering, industrially advantageously, an optically active reagent for optical resolution from a diastereomeric salt of optically active 4-amino-2-methylbutane-1-ol with the optically active reagent for optical resolution.

The present inventors have made extensive study to achieve the above-mentioned objects. As a result, it has been found that optically active 4-amino-2-methylbutane-1-ol can be obtained by reacting, preferably in the presence of a solvent, an optically active organic acid on racemic 4-amino-2-methylbutane-1-ol and then separating thus obtained diastereomeric salt from a mother liquor. This invention was accomplished on the basis of the above finding.

Further, the present inventors have made extensive study to attain the above-mentioned objects. As a result, it has been found that when a diastereomeric salt of optically active 4-amino-2-methylbutane-1-ol with an optically active reagent for optical resolution is contacted with a solvent and an alkali to decompose the salt and the reaction mixture is subjected to solid-liquid separating, optically active 4-amino-2-methylbutane-1-ol can be obtained from a filtrate with a high purity and high yield, and further that the reagent for optical resolution used can be recovered by contacting a filtration residue containing an alkali salt of the reagent for optical resolution obtained by the solid-liquid separation with a solvent and an acid and then subjecting the reagent for optical resolution thus crystallized out to solid-liquid separation. This invention was accomplished on the basis of the above finding.

Further, the present inventors have found that when a salt of optically active 4-amino-2-methylbutane-1ol with an optically active reagent for optical resolution is contacted with a solvent, e.g. an alcohol and water etc., and an alkali, e.g. an alkali metal alcoholate and alkali metal hydroxide etc., to decompose the salt, and the solvent, e.g. an alcohol and water etc., is replaced with an alcohol in which a solubility of an alkali salt (alkali metal salt) of the optically active reagent for optical resolution is low, and an alkali salt (alkali metal salt) of the optically active reagent for optical resolution and a solution of optically active 4-amino-2-methylbutane-1-ol are subjected to solid-liquid separation, the alkali salt (alkali metal salt) of the optically active reagent for optical resolution can be recovered and optically active 4-amino-2-methylbutane-1-ol can be obtained. This invention was accomplished on the basis of the above finding.

Thus, this invention relates to a process for producing optically active 4-amino-2-methylbutane-1-ol which comprises reacting an optically active organic acid on racemic 4-amino-2-methylbutane-1-ol, crystallizing out the resulting diastereomeric salt and subjecting the diastereomeric salt to solid-liquid separation.

Further, this invention relates to a salt of optically active 4-amino-2-methylbutane-1-ol with an optically active organic acid.

Further, this invention relates to a process for producing the above-mentioned salt and to a process for producing optically active 4-amino-2-methylbutane-1-ol by using the salt.

Further, this invention relates to a process for producing optically active 4-amino-2-methylbutane-1-ol which comprises contacting a diastereomeric salt of optically active 4-amino-2-methylbutane-1-ol and an optically active reagent for optical resolution with a solvent and an alkali to decompose the salt, followed by solid-liquid separation to obtain a filtrate, and obtaining optically active 4-amino-2-methylbutane-1-ol from the filtrate.

Further, this invention relates to a process for producing optically active 4-amino-2-methylbutane-1-ol which comprises contacting a filtration residue containing an alkali salt of the optically active reagent for optical resolution obtained by solid-liquid separation in the above-mentioned process with a solvent and an acid, and recovering the thus crystallized optically active reagent for optical resolution by solid-liquid separation.

Further, this invention relates to a process for producing optically active 4-amino-2-methylbutane-1-ol which comprises contacting a diastereomeric salt of optically active 4-amino-2-methylbutane-1-ol and an optically active reagent for optical resolution with a solvent and an alkali to decompose the salt, replacing the solvent with an alcohol in which a solubility of an alkali salt of an optically active reagent for optical resolution is low, and subjecting the alkali salt of the optically active reagent for optical resolution and an optically active 4-amino-2-methylbutane-1-ol solution to solid-liquid separation to recover the alkali salt of the optically active reagent for optical resolution.

Further, this invention relates to a process for producing optically active 4-amino-2-methylbutane-1-ol which comprises contacting a diastereomeric salt of optically active 4-amino-2-methylbutane-1-ol and an optically active reagent for optical resolution with an alcohol and an alkali metal alcoholate to decompose the salt, replacing the alcohol with an alcohol in which a solubility of an alkali metal salt of an optically active reagent for optical resolution is low, and subjecting the alkali metal salt of the optically active reagent for optical resolution and an optically active 4-amino-2-methylbutane-1-ol solution to solid-liquid separation to recover the alkali metal salt of the optically active reagent for optical resolution.

Further, this invention relates to a process for producing optically active 4-amino-2-methylbutane-1-ol which comprises contacting a diastereomeric salt of optically active 4-amino-2-methylbutane-1-ol and an optically active reagent for optical resolution with water and/or an alcohol and an alkali metal hydroxide to decompose the salt, replacing the water and/or alcohol with an alcohol in which a solubility of an alkali metal salt of an optically active reagent for optical resolution is low, and subjecting the alkali metal salt of the optically active reagent for optical resolution and an optically active 4-amino-2-methylbutane-1-ol solution to solid-liquid separation to recover the alkali metal salt of the optically active reagent for optical resolution.

Further, this invention relates to a process for recovering the optically active reagent for optical resolution used in the production of optically active 4-amino-2-methylbutane-1-ol and to a process for producing optically active 4-amino-2-methylbutane-1-ol by reusing the optically active reagent for optical resolution recovered by the recovering process.

Further, this invention relates to a process for using the optically active 4-amino-2-methylbutane-1-ol obtained by the above-mentioned production process as an intermediate for synthesizing optically active medicines and pesticides and to a process for producing optically active medicines or pesticides by using the optically active 4-amino-2-methylbutane-1-ol obtained by the above-mentioned production process.

BEST MODE FOR CARRYING OUT THE INVENTION

Figure 1:
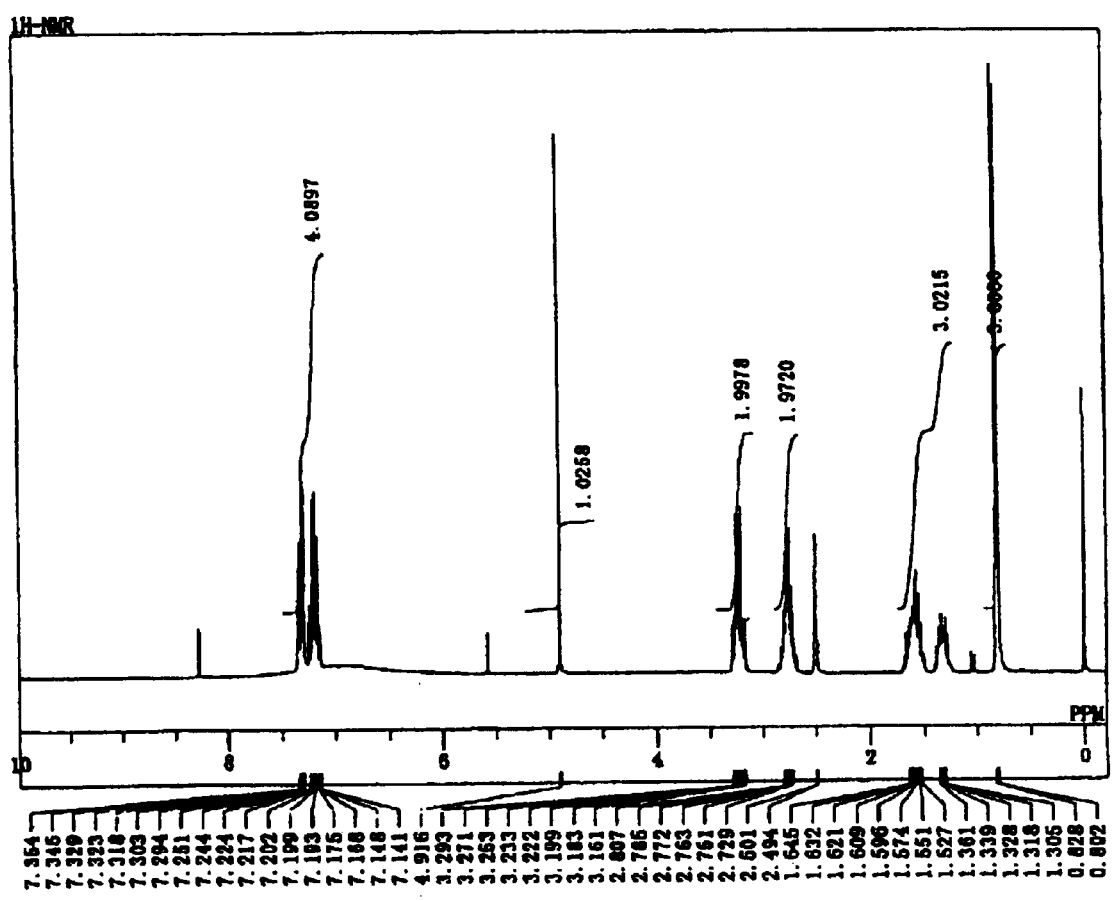
FIG. 1 shows the $^1$H-NMR spectrum of a salt of (R)-2-chloromandelic acid with (R)-4-amino-2-methylbutane-1-ol of this invention.

In the present invention having the above-mentioned essentials, 4-amino-2-methylbutane-1-ol which is the object of optical resolution, has a structure in which a primary hydroxyl group and amino group are present in its molecule, and the asymmetric carbon having a methyl group bonded thereto is at a position corresponding to γ position relative to a carbon having the amino group bonded thereto. The present inventors obtained novel information that a diastereomeric complex of even an amino-alcohol having such a structure with an optically active organic acid (optically active reagent for optical resolution) can be formed, crystallized out and obtained as a salt, and that optically active 4-amino-2-methylbutane-1-ol can be obtained from a filtrate prepared by contacting the salt with a solvent and alkali, followed by solid-liquid separation. Thus, this invention was attained. Further, by obtaining novel information that when an alkali salt of the optically active reagent for optical resolution in a filtration residue obtained by the solid-liquid separation is contacted with a solvent and an acid, and the reaction mixture is subjected to solid-liquid separation, the reagent for optical resolution can be recovered in good yield, this invention was achieved.

Further, this invention was attained by obtaining novel information that when a salt of optically active 4-amino-2-methylbutane-1-ol with an optically active reagent for optical resolution is contacted with a solvent, e.g. an alcohol and water etc., and an alkali, e.g. an alkali metal alcoholate and alkali metal hydroxide etc., to decompose, the solvent, e.g. an alcohol and water etc., is replaced with an alcohol in which a solubility of an alkali salt (alkali metal salt) of the optically active reagent for optical resolution is low, and the alkali salt (alkali metal salt) of the optically active reagent for optical resolution and an optically active 4-amino-2-methylbutane-1-ol solution are subjected to solid-liquid separation, the optically active organic acid can be recovered and optically active 4-amino-2-methylbutane-1-ol can be obtained in good yield.

The optically active organic acid usable in this invention may be various reagent for optical resolutions of a natural origin or of a synthetic product and may be of both the R-configuration and the S-configuration thereof. Preferred examples thereof include optically active carboxylic acids, optically active sulfonic acids and optically active phosphonic acids represented by the formula (1)

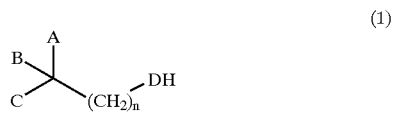

(1)

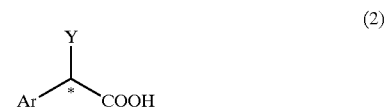

(2)

wherein D denotes COO⁻, SO₃⁻ or PO₃H⁻; A, B and C each denote hydrogen, a substituted or unsubstituted, straight or branched chain alkyl group having 1–10 carbon atoms, halogen atom, alkoxy group, hydroxyl group, nitro group, carboxyl group, acyloxy group, or substituted or unsubstituted amino group, phenyl group or naphthyl group; the substituent in the alkyl group, amino group, phenyl group or naphthyl group is a straight or branched chain alkyl group having 1–10 carbon atoms, halogen atom, alkoxy group, hydroxyl group, nitro group, benzoyl group, carboxyl group, acyl group, methylthio group or sulfonic acid group; provided that A, B, C and (CH₂)n-DH are not the same with each other at the same time, and n is 1 or 0.

In the optically active carboxylic acid, optically active sulfonic acid or optically active phosphonic acid represented by the formula (1), the straight or branched chain alkyl group having 1–10 carbon atoms denoted by A, B or C may be, for example, methyl group, ethyl group, n-propyl group, isopropyl group, n-butyl group, sec-butyl group, tert-butyl group, isobutyl group, pentyl group, hexyl group, octyl group or cyclohexyl group. The halogen atom may be, for example, fluorine, chlorine or bromine atom. The alkoxy group may be, for example, methoxy group, ethoxy group or propoxy group. The acyloxy group may be, for example, acetyloxy group. The substituent in the above-mentioned alkyl group, amino group, phenyl group or naphthyl group may be, for example, the above-mentioned straight or branched chain alkyl group having 1–10 carbon atoms, halogen atom, alkoxy group, hydroxyl group, nitro group, benzoyl group, carboxyl group, acyl group such as acetyl group, methylthio group or sulfonic acid group etc.

Specific examples of the optically active carboxylic acid include optically active hydroxycarboxylic acids such as tartaric acid, malic acid, lactic acid, mandelic acid, dibenzoyltartaric acid, citramalic acid, phenyllactic acid, pantothenic acid and 1,4-benzodioxane-2-carboxylic acid, and derivatives of the hydroxycarboxylic acid; 2-bromopropionic acid, γ-carboxy-γ-butyrolactone, 2-chlorobutanoic acid, 2-methylhexanoic acid, 2-methyldecanoic acid, 2-methylbutanoic acid, menthyloxyacetic acid, tetrahydrofuroic acid, 2-phenylbutanoic acid, 2-phenylpropionic acid, 2-phenylsuccinic acid, optically active N-substituted amino acid, pyroglutamic acid, camphoric acid and N-acetyl-(D)-valine.

The optically active organic sulfonic acid may be, for example, 10-camphorsulfonic acid, phenylethanesulfonic acid, α-bromocamphor-ρ-sulfonic acid or 3-endobromocamphor-8-sulfonic acid. The optically active organic phosphonic acid may be, for example, 1-amino-2-methylpropionylphosphonic acid.

Particularly preferred among the optically active carboxylic acids represented y the formula (1) includes an optically active 2-aryl-2-substituted acetic acid represented by the formula (2).

wherein Y denotes a straight or branched chain alkyl group having 1–10 carbon atoms, halogen atom, alkoxy group, acyloxy group or hydroxyl group; Ar denotes a substituted or unsubstituted phenyl group or naphthyl group; the substituent is a straight or branched chain alkyl group having 1–10 carbon atoms, halogen atom, alkoxy group, hydroxyl group, nitro group, benzoyl group, carboxyl group, methylthio group or sulfonic acid group; and * denotes asymmetric carbon.

In the optically active 2-aryl-2-substituted acetic acid represented by the above formula (2), specific examples of the straight or branched chain alkyl group having 1–10 carbon atoms, halogen atom, alkoxy group and acyloxy group denoted by Y include those exemplified in the above-mentioned formula (1). The group Ar may be for example, a substituted or unsubstituted phenyl group or naphthyl group, and the substituent therein is, for example, the above-mentioned straight or branched chain alkyl group having 1–10 carbon atoms, halogen atom, alkoxy group, hydroxyl group, nitro group, carboxyl group and sulfonic acid group.

Specific examples of the optically active 2-aryl-2-substituted acetic acid include o-acetylmandelic acid.

Particularly preferable examples of the above-mentioned optically active 2-aryl-2-substituted acetic acids represented by the formula (2) include optically active mandelic acid derivatives represented by the following formula (3).

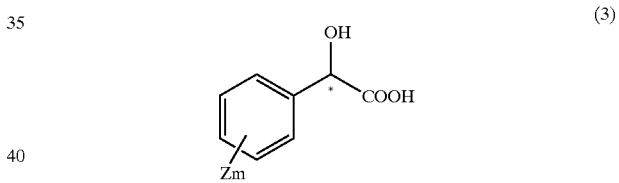

(3)

wherein Z denotes hydrogen or a straight or branched chain alkyl group having 1–10 carbon atoms, halogen atom, alkoxy group, hydroxyl group, nitro group, methylthio group or benzoyl group; * denotes asymmetric carbon; m is an integer of 1–5; and when m≧2, z may be the same or different.

In the optically active mandelic acid derivative represented by the above formula (3), specific examples of the straight or branched chain alkyl group having 1–10 carbon atoms, halogen atom and alkoxy group denoted by Z include those exemplified in the above formula (1). Herein, Z is preferably hydrogen, methyl group, ethyl group, fluorine atom, chlorine atom, bromine atom, methoxy group, ethoxy group, hydroxyl group, methylthio group or nitro group, more preferably hydrogen, chlorine atom or nitro group.

The optically active mandelic acid derivative represented by the above formula (3) is preferably mandelic acid, 2-chloromandelic acid, 3-chloromandelic acid, 4-chloromandelic acid, 2-bromomandelic acid, 3-bromomandelic acid, 4-bromomandelic acid, 2-hydroxymandelic acid, 3-hydroxymandelic acid, 4-hydroxymandelic acid, 2-methylmandelic acid, 3-methylmandelic acid, 4-methylmandelic acid, 2-methoxymandelic acid, 3-methoxymandelic acid, 4-methoxymandelic acid, 2-nitromandelic acid, 3-nitromandelic acid, 4-nitromandelic acid or methylthiomandelic acid, more preferably mandelic acid, 2-chloromandelic acid, 4-chloromandelic acid or 4-nitromandelic acid.

The method of preparation of these optically active mandelic acid derivatives is not particularly limited and may be, for example, those described in JP-A-4-99496 and JP-A-4-222591.

In this invention, the solvents which can be used in reacting an optically active organic acid on racemic 4-amino-2-methylbutane-1-ol are not particularly limited, but they are preferably water; various alcohols such as methanol, ethanol, isopropanol, n-propanol and butanol; ethers such as diethyl ether, isopropyl ether, tetrahydrofuran and dioxane: ketones such as acetone and methyl ethyl ketone; esters such as methyl acetate and ethyl acetate; nitrogen-containing solvent such as acetonitrile and dimethylformamide; halogenated hydrocarbons such as dichloromethane, dichloroethane and chloroform; or a mixed solvent thereof. More preferably used are water, methanol, ethanol, isopropanol, n-propanol, isopropyl ether, acetone, acetonitrile, or a mixed solvent thereof.

In this invention, the method used for forming the diastereomeric salt in a solvent is not particularly limited. For example, the diastereomeric salt may be formed by dissolving the optically active organic acid used as the reagent for optical resolution in a suitable solvent as described above and then dropwise adding thereto an equimolar amount of racemic 4-amino-2-methylbutane-1-ol directly or after having been diluted with a suitable solvent, or alternatively the reactants may be mixed in the reverse order. The mixing temperature is not particularly limited but it is preferably 0–100° C., more preferably 10–80° C. The molar ratio of the optically active organic acid to racemic 4-amino-2-methylbutane-1-ol used is not particularly limited, but it is preferably 0.2–5, more preferably 0.5–2. When the reactants are dissolved in a solvent, the concentrations of the optically active organic acid and racemic 4-amino-2-methylbutane-1-ol are not particularly limited, but they are respectively preferably 0.1–80% (by weight), more preferably 1–50% (by weight). The diastereomeric salt solution thus obtained can be cooled, directly or after having been concentrated, to deposit crystals. In this instance, a small amount of a crystal of a diastereomeric salt having a high optical purity can be added as a seed crystal thereby to effect a more efficient crystallization. Though the optical purity of the seed crystal is preferably high, the amount thereof to be added is sufficient when it is about 0.01–1% of the amount of solute. Even when utterly no seed crystal is added, the crystallization of the diastereomeric salt occurs spontaneously if the salt is in the state of super saturation, and the diastereomeric salt can be deposited as well as in the case where seed crystal is added. From a mother liquor obtained after separation of crystals, a salt of enantimorphic 4-amino-2-methylbutane-1-ol can be recovered through such an operation as concentration. Accordingly, any desired optical isomer can be obtained.

The diastereomeric salt thus obtained can be recrystallized by using a suitable solvent, e.g., ethanol or the like, as described above, to obtain an optically purer diastereomeric salt. The diastereomeric salt can be neutralized or treated with anion exchange resin to recover an optically active amino-alcohol. The optically active organic acid used as the reagent for optical resolution can be recovered and reused.

Examples of the salt of optically active 4-amino-2-methylbutane-1-ol with an optically active organic acid (optically active reagent for optical resolution) of this invention include the salts of optically active 4-amino-2-methylbutane-1-ol with an optically active carboxylic acid, optically active sulfonic acid or optically active phosphonic acid represented by the following formula (4)

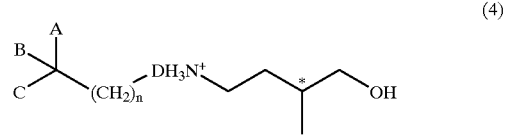

(4)

wherein the definition and specific examples of A, B, C, D and n are the same as in the formula (1), and * denotes asymmetric carbon.

Specific examples of the optically active carboxylic acid, optically active sulfonic acid or optically active phosphonic acid are the same as those exemplified in the formula (1).

Preferred among the above-mentioned salts represented by the formula (4) include salts of an optically active 2-aryl-2-substituted acetic acid with optically active 4-amino-2-methylbutane-1-ol represented by the following formula (5).

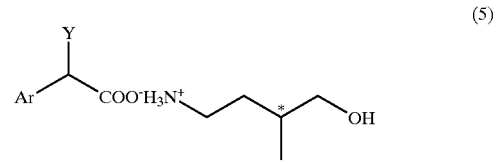

(5)

wherein the definition and specific examples of Ar and Y are the same as in the formula (2), and * denotes asymmetric carbon.

Specific examples of the optically active 2-aryl-2-substituted acetic acid in the formula (5) include the same as those exemplified in the above formula (2).

More preferred among the above-mentioned salts represented by the formula (4) include salts of an optically active mandelic acid derivative with optically active 4-amino-2-methylbutane-1-ol represented by the following formula (6).

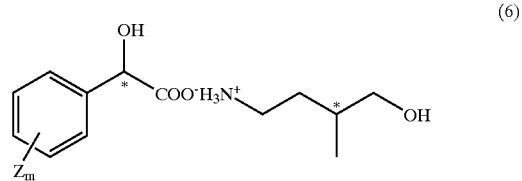

(6)

wherein the definition and specific examples of Z and m are the same as those exemplified in the formula (3).

Specific examples of the optically active mandelic acid derivative in the formula (6) include the same as those exemplified in the above formula (3).

In the process of this invention, optically active 4-amino-2-methylbutane-1-ol can be obtained by contacting the diastereomeric salt obtained as described above with a solvent and an alkali to decompose the salt, cooling the reaction mixture, then subjecting the mixture to solid-liquid separation and subjecting the resulting filtrate to operations such as concentration, distillation under reduced pressure and the like.

Alkalis used at this time are preferably alkali metal hydroxides, alkaline earth metal hydroxides, alkali metal alcoholates, alkaline earth metal alcoholates or ammonia, more preferably alkali metal hydroxides or alkali metal alcoholates, and still more preferably sodium hydroxide, potassium hydroxide, lithium hydroxide or alcoholates of an alcohol, such as methanol and ethanol, with sodium, potassium or the like. The amount of the alkali used is preferably 0.5–3 equivalents, more preferably 0.9–1.1 equivalents, relative to the diastereomeric salt.

The solvents used to be contacted with the diastereomeric salt are not particularly limited, but they include preferably water, various alcohols, such as methanol, ethanol, isopropanol, n-propanol and butanol, ethers, such as diethyl ether, isopropyl ether, tetrahydrofuran, dioxane and methyl tert-butyl ether, ketones, such as acetone and methyl ethyl ketone, esters, such as methyl acetate and ethyl acetate, nitrogen-containing solvents, such as acetonitrile and dimethylformamide, and a mixture thereof. More preferably used include water, various alcohols, such as methanol, ethanol, isopropanol, n-propanol and butanol, and a mixture thereof.

The method of contact is not particularly limited. It may be conducted, for example, by adding a diastereomeric salt into a solvent and, at a state wherein at least a part of the diastereomeric salt is dissolved, adding to the resulting mixture, with stirring, an alkali in the form of powder or granules, suspension or solution. The temperature is usually from a melting point to a boiling point of the solution, preferably from 30° C. to a boiling point. The amount of the solvent, which may be used in as small an amount as possible since separated mother liquor can be recycled, is preferably 0.1 time–100 times (by weight), more preferably 1 time–5 times (by weight), the amount of the diastereomeric salt.

To promote the crystallization of the alkali salt of the optically active reagent for optical resolution, such operations as cooling and concentration may be conducted. The temperature after the cooling is preferably from the melting point of the solvent to 30° C., more preferably 0–15° C. The method for solid-liquid separation of the alkali salt of organic acid and the mother liquor is not particularly limited; for example, the separation can be conducted by filtration or sedimentation. For the filtration, centrifugal filtration, pressure filtration or vacuum filtration can be used. Filtration residue obtained by solid-liquid separation may be washed with a solvent if desired.

By heating and concentrating the solution obtained by solid-liquid separation, a high concentration solution of optically active 4-amino-2-methylbutane-1-ol can be obtained. The concentration is conducted usually under normal or reduced pressure preferably at 30–120° C. By conducting, if necessary, simple distillation or rectification, a high purity optically active 4-amino-2-methylbutane-1-ol can be obtained. The conditions of distillation is not particularly limited, but it is preferably conducted under a vacuum of 1–120 Torr at a temperature of 50–200° C., more preferably 60–150° C.

The filtration residue obtained by solid-liquid separation mentioned above is contacted with a solvent and an acid, then cooled, and the precipitate is subjected to solid-liquid separation, whereby the optically active reagent for optical resolution can be recovered.

The solvents used at this time are not particularly limited, but they are preferably water, various alcohols, such as methanol, ethanol, isopropanol, n-propanol and butanol, ethers, such as diethyl ether, isopropyl ether, tetrahydrofuran and dioxane, ketones, such as acetone and methyl ethyl ketone, or a mixture thereof, more preferably water, various alcohols, such as methanol, ethanol, iso-propanol, n-propanol and butanol, or a mixture thereof.

The acid which can be used includes mineral acids, such as hydrochloric acid, nitric acid or sulfuric acid. When the solvent is water, the pH after addition of the acid is preferably not higher than 3, more preferably 1–2. The temperature at the time of solid-liquid separation is preferably not higher than 40° C., more preferably 0–15° C.

The method of contact is not particularly limited. For example, it may be conducted by adding the alkali salt of an optically active reagent for optical resolution into a solvent, dissolving at least a part of the salt, and adding an acid to the resulting mixture with stirring. The temperature is usually from the melting point to the boiling point of the solution, preferably from 30° C. to the boiling point. The amount of the solvent, which may be used in as small an amount as possible since separated mother liquor can be recycled, is preferably 0.1 time–100 times (by weight), more preferably 1 time–5 times (by weight) the amount of the alkali salt of the optically active reagent for optical resolution. To promote the crystallization of the optically active reagent for optical resolution, such operations as cooling and concentration may be conducted. The temperature after the cooling is preferably from the melting point of the solvent to 40° C., more preferably 0–15° C.

The method for solid-liquid separation of the optically active reagent for optical resolution and the mother liquor is not particularly limited; for example, the separation can be conducted by filtration or sedimentation. For the filtration, centrifugal filtration, pressure filtration or vacuum filtration can be used. Filtration residue obtained by solid-liquid separation may be washed with a solvent if desired.

In the process of this invention, the diastereomeric salt of optically active 4-amino-2-methylbutane-1-ol with an optically active reagent for optical resolution is contacted with a solvent, such as alcohol, and an alkali, such as alkali metal alcoholate, to decompose the salt, then the solvent, such as alcohol, is replaced with an alcohol in which a solubility of an alkali salt (alkali metal salt) of the optically active reagent for optical resolution is low, and the alkali salt (alkali metal salt) of the optically active reagent for optical resolution and an optically active 4-amino-2-methylbutane-1-ol solution are subjected to solid-liquid separation, whereby an optically active 4-amino-2-methylbutane-1-ol solution, in which the concentration of the alkali salt (alkali metal salt) of the optically active reagent for optical resolution is low, can be obtained. By subjecting the solution to such an operation as concentration or distillation, a high purity optically active 4-amino-2-methylbutane-1-ol can be produced in high yield.

The solvent used to be contacted with the diastereomeric salt in the above-mentioned process is not particularly limited as described above, but, as specific examples thereof, can include alcohols, particularly methanol, ethanol and the like. Examples of the alcohols, in which a solubility of the alkali salt (alkali metal salt) of the optically active reagent for optical resolution is low, include isopropyl alcohol, n-butanol, 2-butanol and t-butanol.

Examples of the alkali to be contacted with the diastereomeric salt are the same as described above. Examples of the alkali metal alcoholate include alcoholates of alcohols, such as methanol and ethanol, with sodium, potassium and the like. The amount of the alkali metal alcoholate used is preferably 0.5–3 equivalents, more preferably 0.9–1.1 equivalents relative to the diastereomeric salt.

The method of contacting is not particularly limited. It may be conducted by adding a diastereomeric salt to an alcohol, dissolving at least a part of the salt, and adding to the resulting mixture, with stirring, an alkali metal alcoholate in the form of powder or granules, suspension or alcoholic solution. The temperature is usually from the melting point to the boiling point of the solution, preferably from 30° C. to the boiling point. The amount of the solvent, which may be used in as small an amount as possible since separated mother liquor can be recycled, is preferably 0.1 time–100 times (by weight), more preferably 1 time–5 times (by weight) the amount of the diastereomeric salt.

To promote the crystallization of the alkali metal salt of the optically active reagent for optical resolution, such operations as cooling, concentration and replacing with a solvent having low solubility may be conducted. The temperature after the cooling is preferably from the melting point of the solvent to 30° C., more preferably 0° C.–15° C. "Displacement concentration" may also be conducted. Then term "Displacement concentration" refers to an operation which comprises adding to the reaction mixture a solvent, in which a solubility of an alkali salt of an organic acid (reagent for optical resolution) is low, while concentrating the mixture, thereby to replace the solvent and to promote the crystallization of the alkali salt of the organic acid.

The method for solid-liquid separation of the alkali metal salt of the optically active reagent for optical resolution and the mother liquor is not particularly limited; for example, the separation can be conducted by filtration or sedimentation. For the filtration, centrifugal filtration, pressure filtration or vacuum filtration can be used. Filtration residue obtained by solid-liquid separation may be washed with a solvent if desired. By heating and concentrating the solution obtained by solid-liquid separation, a high concentration solution of optically active 4-amino-2-methylbutane-1-ol can be obtained. The concentration is conducted, usually, under normal or reduced pressure preferably at 30–120° C. By conducting simple distillation or rectification according to necessity, a high purity optically active 4-amino-2-methylbutane-1-ol can be obtained. The distillation is preferably conducted under a vacuum of 1–120 Torr at a temperature of 50–200° C., more preferably 60–150° C.

The alkali salt (alkali metal salt) of the optically active reagent for optical resolution thus obtained is contacted with a solvent and an acid according to the same method as described above, and the resulting precipitate is separated by solid-liquid separation or subjected to other suitable procedure, whereby the optically active reagent for optical resolution can be recovered.

According to the process of this invention, a diastereomeric salt of optically active 4-amino-2-methylbutane-1-ol with an optically active reagent for optical resolution is contacted with water and/or alcohol and an alkali metal hydroxide to decompose the salt, then water and/or alcohol are replaced with an alcohol, such as butanol, in which a solubility of an alkali metal salt of the optically active reagent for optical resolution is low, and the alkali metal salt of the optically active reagent for optical resolution and an optically active 4-amino-2-methylbutane-1-ol solution are subjected to solid-liquid separation, whereby an optically active 4-amino -2-methylbutane-1-ol solution in which the concentration of the alkali metal salt of the optically active reagent for optical resolution is low can be obtained. The solution thus obtained can be subjected to such operations as concentration and distillation to produce a high purity optically active 4-amino-2-methylbutane-1-ol in high yield.

Examples of the alcohol to be contacted with the diastereomeric salt in the above-mentioned process are the same as described above and include, particularly, methanol, ethanol and the like. The alcohol, in which a solubility of an alkali metal salt of the optically active reagent for optical resolution is low, can include isopropyl alcohol, n-butanol, 2-butanol, t-butanol and the like.

The alkali metal hydroxide used is preferably sodium hydroxide, potassium hydroxide and lithium hydroxide, more preferably sodium hydroxide. The amount of the alkali metal hydroxide used is preferably 0.5–3 equivalents, more preferably 0.9–1.1 equivalents, relative to the diastereomeric salt.

The method of contact is not particularly limited; it may be conducted by adding a diastereomeric salt into a solvent, dissolving at least a part of the salt, and adding to the resulting mixture, with stirring, an alkali metal hydroxide in the form of powder or granules, suspension or solution. The temperature is usually from the melting point to the boiling point of the solution, preferably from 30° C. to the boiling point. The amount of the solvent, which may be used in as small an amount as possible since separated mother liquor can be recycled, is preferably 0.1 time–100 times (by weight), more preferably 1 time–5 times (by weight) the amount of the diastereomeric salt.

To promote the crystallization of the alkali metal salt of the optically active reagent for optical resolution, such operations as cooling, concentration and replacing with a solvent having low solubility can be conducted. The concentration is usually conducted by heating under normal or reduced pressure preferably at 30–120° C. If necessary, cooling can be conducted. The temperature after cooling is preferably from the melting point of the solvent to 30° C., more preferably 0° C.–15° C.

By conducting such operations as replacing water and/or alcohol with a solvent having low solubility, the crystallization of the alkali metal salt of the reagent for optical resolution can be promoted. Replacement with a solvent having low solubility may be conducted by a method of displacement concentration, which comprises adding a solvent in which a solubility of an alkali metal salt of the optically active reagent for optical resolution is low while conducting concentration, or by a method of adding a solvent having low solubility after concentration.

The solid-liquid separation of the alkali metal salt of the optically active reagent for optical resolution and the mother liquor may be conducted by any desired method, for example by filtration or sedimentation. For the filtration, centrifugal filtration, pressure filtration or vacuum filtration may be used. Filtration residue obtained by the solid-liquid separation may be washed with a solvent if necessary.

The alkali metal salt of the optically active reagent for optical resolution thus obtained is contacted with a solvent and an acid according to the same method as described above, and precipitate obtained is separated by solid-liquid separation, whereby the optically active reagent for optical resolution can be recovered.

As the diastereomeric salt of optically active 4-amino-2-methylbutane-1-ol with an optically active reagent for optical resolution used in the above-mentioned process of this invention, there may be mentioned those represented by the above-mentioned formula (4), (5) or (6).

In this way, a diastereomeric salt of optically active 4-amino-2-methylbutane-1-ol with an optically active reagent for optical resolution (optically active organic acid) can be produced, and optically active 4-amino-2-methylbutane-1-ol can be produced by using the diastereomeric salt. Further, the optically active reagent for optical resolution used in the production of optically active 4-amino-2-methylbutane-1-ol can be recovered, and the optically active reagent for optical resolution thus recovered can be reused to produce optically active 4-amino-2-methylbutane-1-ol. Further, the optically active 4-amino-2-methylbutane-1-ol thus obtained can be used as an intermediate for synthesizing optically active medicines or pesticides, and optically active medicines or pesticides can be produced by using the optically active 4-amino-2-methylbutane-1-ol thus obtained.

This invention is described in detail below with reference to Examples, but the scope of the invention is in no way limited to the scope of the Examples.

EXAMPLE 1

In 10 ml of isopropanol was dissolved 1.86 g of (R)-2-chloromandelic acid, then 1.03 g of racemic 4-amino-2-methylbutane-1-ol was dropwise added thereto, and the resulting mixture was heated to form a solution. The solution was cooled to room temperature, 1 mg of a salt of (R)-2-chloromandelic acid with (R)-4-amino-2-methylbutane-1-ol was added thereto as a seed crystal, and further cooled gradually to 5° C. Precipitated crystal was separated by filtration and rinsed with cold isopropanol to obtain 1.61 g of diastereomeric salt crystal. The optical purity of 4-amino-2-methylbutane-1-ol in the crystal was (R)-isomer 63% e.e. The crystal was dissolved by heating in 10 ml of isopropanol and subjected to repeated recrystallization to obtain 0.95 g of diastereomeric salt crystal of high optical purity. The optical purity of 4-amino-2-methylbutane-1-ol in the crystal was R-isomer 99.9% e.e. The characteristic properties of the crystal are shown below.

The optical purity of 4-amino-2-methylbutane-1-ol in the crystal was determined by converting the crystal into a dibenzoyl derivative as described below. That is, 0.29 g of the diastereomeric salt crystal was dissolved in 2 ml of 1N NaOH and extracted three times with an equal amount of tetrahydrofuran. An organic phase was concentrated under vacuum to obtain 0.09 g of optically active 4-amino-2-methylbutane-1-ol. An about 20 mg portion thereof was weighed out, then 1 ml of methylene chloride, 60 mg of pyridine and 60 mg of benzoyl chloride were added thereto in said order, and the resulting mixture was allowed to react at room temperature for 10 minutes. Thereafter, 2 ml of methylene chloride was added thereto, the resulting mixture was washed twice with 2 ml of 1N hydrochloric acid, once with 2 ml of 10% aqueous sodium carbonate solution and once with 2 ml of water, and an organic layer was concentrated to obtain 60 mg of a dibenzoyl derivative. HPLC analysis made under the following conditions showed that S-isomer was eluted at 42.4 minute and R-isomer at 54.3 minute, and the degree of separation was 3.2. The optical purity was calculated from the ratio of peak areas of the S-isomer and the R-isomer in the HPLC chart obtained.

Liquid Chromatography Conditions

Column: Chiral cell OD, mfd. by Daicel Chemical Industries, Ltd.
Mobile phase: hexane/isopropyl alcohol=90/10
Flow rate: 0.5 ml/min
Column temperature: room temperature
Detection: UV 254 nm Characteristic properties of a salf of (R)-2-chloromandelic acid with (R)-4-amino-2-methylbutane-1-ol
<Crystal form> needle crystal
<Specific rotation>
$[\alpha]_D^{26} = -62.24$ (c = 2.01, MeOH)
<Melting point>
126.6–127.6° C.

-continued

<¹H-NMR spectrum> DMSO, internal standard TMS (FIG. 1)

| | | |
|---|---|---|
| $\delta^H$ | 0.802–0.828 | (3H, d, —CH$_3$) |
| $\delta^H$ | 1.305–1.339 | (1H, m, —CH$_2$) |
| $\delta^H$ | 1.596 | (2H, m, —CH$_2$, —CH) |
| $\delta^H$ | 2.729 | (2H, m, —CH$_2$) |
| $\delta^H$ | 3.222–3.253 | (2H, dq, —CH$_2$) |
| $\delta^H$ | 4.916 | (1H, s, —CH) |
| $\delta^H$ | 7.302–7.345 | (4H, m, C$_6$H$_4$—) |

Figure 2:
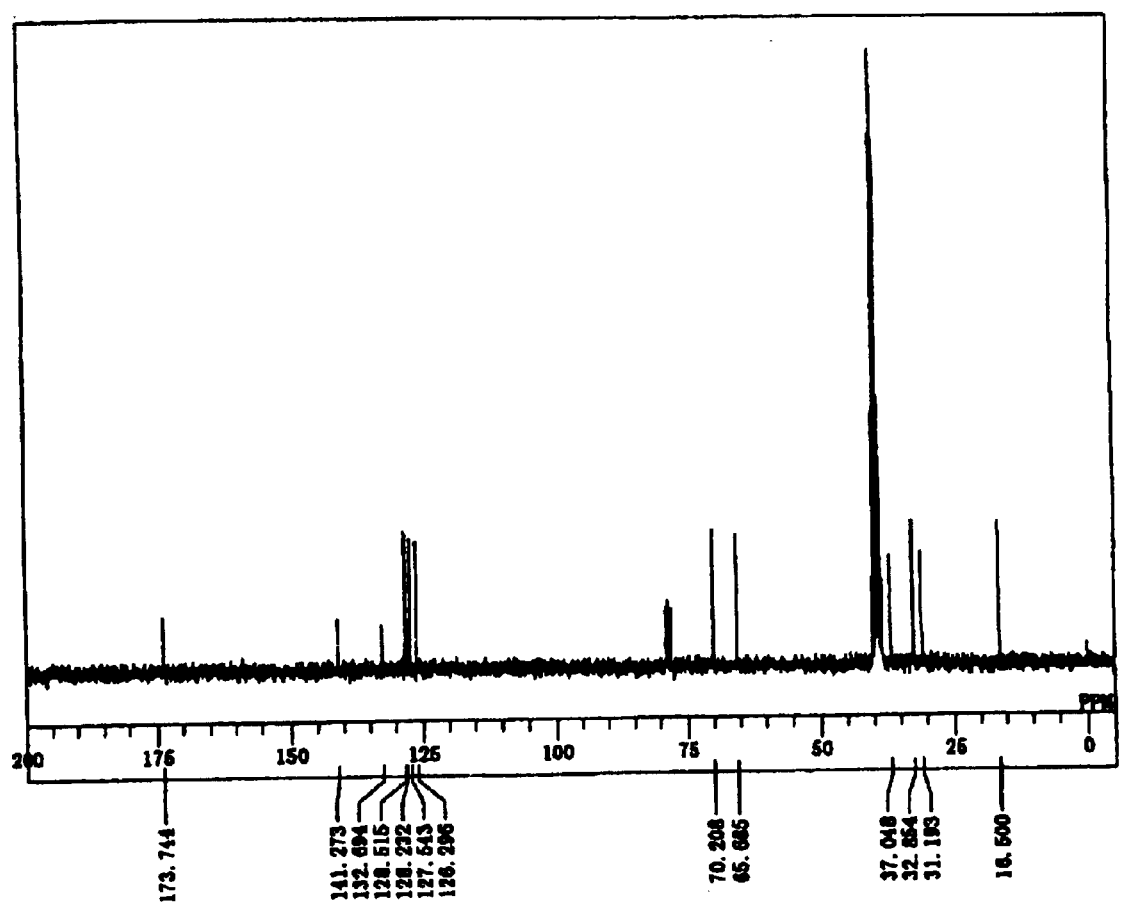
FIG. 2 shows the $^{13}$C-NMR spectrum of a salt of (R)-2-chloromandelic acid with (R)-4-amino-2-methylbutane-1-ol of this invention.

<¹³C-NMR spectrum> DMSO, internal standard TMS (FIG. 2)

| | | |
|---|---|---|
| $\delta^C$ | 16.526 | (—Ch$_2$OH) |
| $\delta^C$ | 31.220 | (—CH$_2$) |
| $\delta^C$ | 32.880 | (—CH) |
| $\delta^C$ | 37.074 | (—CH$_2$) |
| $\delta^C$ | 65.711 | (—CH$_2$) |
| $\delta^C$ | 70.234 | (—CH) |
| $\delta^C$ | 126.322, 127.570, 128.258, 128.542, 132.720, 141.299 | (C$_6$H$_4$—) |
| $\delta^C$ | 173.770 | (—COO) |

Figure 3:
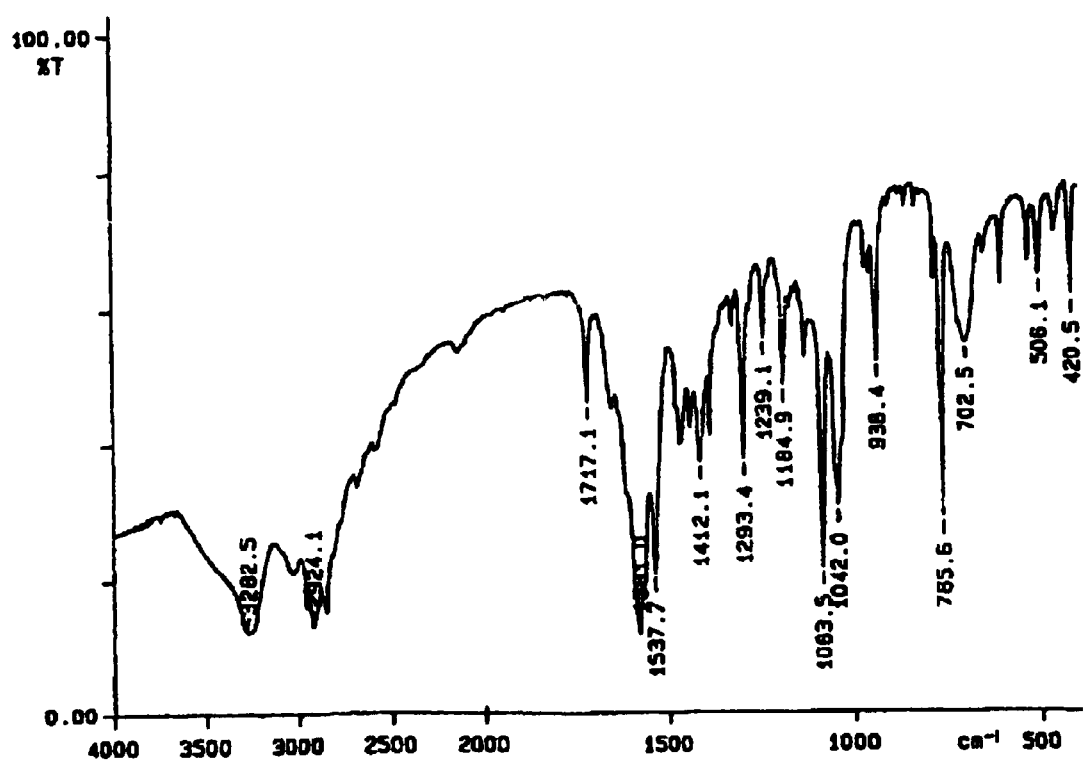
FIG. 3 shows the IR spectrum of a salt of (R)-2-chloromandelic acid with (R)-4-amino-2-methylbutane-1-ol of this invention.

<IR spectrum> KBr tablet method (FIG. 3)

| | |
|---|---|
| O-H stretching | 3283 cm$^{-1}$ |
| N-H stretching | 2924 cm$^{-1}$ |
| COO antisymmetric stretching | 1581 cm$^{-1}$ |
| C-N stretching | 1084 cm$^{-1}$ |

EXAMPLE 2

In exactly the same manner as in Example 1 except for changing the solvent used to ethanol and conducting no-recrystallization, 1.25 g of diastereomeric salt crystal was obtained. The optical purity of optically active 4-amino-2-methylbutane-1-ol in the crystal was (R)-isomer 75.4% e.e.

EXAMPLE 3

In exactly the same manner as in Example 1 except for changing the solvent used to acetone and conducting no recrystallization, 0.34 g of diastereomeric salt crystal was obtained. The optical purity of optically active 4-amino-2-methylbutane-1-ol in the crystal was (R)-isomer 85.5% e.e.

EXAMPLE 4

In exactly the same manner as in Example 1 except for changing the solvent used to n-propanol and conducting no recrystallization, 1.32 g of diastereomeric salt crystal was obtained. The optical purity of optically active 4-amino-2-methylbutane-1-ol in the crystal was (R)-isomer 69.9% e.e.

EXAMPLE 5

In exactly the same manner as in Example 1 except for changing the solvent used to acetonitrile and conducting no recrystallization, 1.33 g of diastereomeric salt crystal was obtained. The optical purity of optically active 4-amino-2-methylbutane-1-ol in the crystal was (R)-isomer 29.2% e.e.

EXAMPLE 6

In exactly the same manner as in Example 1 except for changing the solvent used to isopropyl ether and conducting no recrystallization, 2.74 g of diastereomeric salt crystal was obtained. The optical purity of optically active 4-amino-2-methylbutane-1-ol in the crystal was (R)-isomer 9.3% e.e.

EXAMPLE 7

In exactly the same manner as in Example 1 except for changing the optically active organic acid used to (R)-4- chloromandelic acid, changing the seed crystal to a salt of (R)-4-chloromandelic acid with (R)-4-amino-2-methylbutane-1-ol and conducting no recrystallization, 0.34 g of diastereomeric salt crystal was obtained. The optical purity of optically active 4-amino-2-methylbutane-1-ol in the crystal was (R)-isomer 9.6% e.e.

EXAMPLE 8

In exactly the same manner as in Example 1 except for changing the optically active organic acid used to (R)-4-nitromandelic acid, changing the seed crystal to a salt of (R)-4-nitromandelic acid with (R)-4-amino-2-methylbutane-1-ol and conducting no recrystallization, 1.32 g of diastereomeric salt crystal was obtained. The optical purity of optically active 4-amino-2-methylbutane-1-ol in the crystal was (R)-isomer 86.6% e.e.

EXAMPLE 9

In exactly the same manner as in Example 1 except for changing the optically active organic acid used to (S)-2-chloromandelic acid, changing the seed crystal to a salt of (S)-2-chloromandelic acid with (S)-4-amino-2-methylbutane-1-ol and conducting no recrystallization, 1.53 g of diastereomeric salt crystal was obtained. The optical purity of optically active 4-amino-2-methylbutane-1-ol in the crystal was (S)-isomer 75.9% e.e. Further, the crystal was dissolved by heating in 10 ml of isopropanol and subjected to repeated recrystallization operation to obtain 0.82 g of a diastereomeric salt crystal of high optical purity. The optical purity of 4-amino-2-methylbutane-1-ol in the crystal was (S)-isomer 99.9% e.e. The characteristic properties of the crystal are shown below.
Characteristic properties of a salt of (S)-2-chloromandelic acid with (S)-4-amino-2methylbutane-1-ol
  <Crystal Form>
  Needle crystal
  <Specific Rotation>
  $[\alpha]_D^{26}=:60.11$ (c=2.03, MeOH)
  <Melting Point>
  123.6–124.0° C.

EXAMPLE 10

In 1100 ml of isopropanol was dissolved 200 g of (R)-2-chloromandelic acid, 110 g of racemic 4-amino-2-methylbutane-1-ol was dropwise added thereto, and the resulting mixture was heated to form a solution. The solution was cooled to room temperature, then 100 mg of a salt of (R)-2-chloromandelic acid with (R)-4-amino-2-methylbutane-1-ol was added thereto as a seed crystal, and the resulting mixture was further cooled gradually to 5° C. Deposited crystal was separated by filtration and rinsed with cold isopropanol to obtain 173 g of diastereomeric salt crystal. The optical purity of 4-amino-2-methylbutane-1-ol in the crystal was (R)-isomer 63% e.e. Further, the crystal was dissolved by heating in 1,100 ml of isopropanol, and subjected to repeated recrystallization operation to obtain 102 g of a diastereomeric salt crystal having high optical purity. The optical purity of 4-amino-2-methylbutane-1-ol in the crystal was (R)-isomer 99.9% e.e.

EXAMPLE 11

In 415 g of methanol was dissolved, with heating, 100 g of the diastereomeric salt crystal of high optical purity obtained in Example 10, then 80 g of a 28% sodium methylate methanol solution was added thereto to decompose the salt, the resulting reaction mixture was cooled to 5° C., and then subjected to solid-liquid separation. The separated solution was concentrated, and then distilled in vacuo to obtain 15 g of (R)-4-amino-2-methylbutane-1-ol. The optical purity of (R)-4-amino-2-methylbutane-1-ol obtained was 99.9% e.e. Filtration residue obtained by the solid-liquid separation was dissolved by heating in 80 g of water, 7 g of concentrated sulfuric acid was added thereto, the resulting mixture was cooled to 5° C. and subjected to solid-liquid separation. The amount of recovered (R)-2-chloromandelic acid was 22 g.

EXAMPLE 12

In 415 g of methanol was dissolved, with heating, 100 g of a diastereomeric salt crystal having high optical purity obtained in the same manner as in Example 10, 80 g of a 28% sodium methylate methanol solution was added thereto to decompose the salt, then the resulting reaction mixture was cooled to 5° C. and subjected to solid-liquid separation. The separated solution was concentrated, isopropanol was added thereto, the resulting mixture was subjected to solid-liquid separation, the solution thus obtained was concentrated and then distilled in vacuo to obtain 28 g of (R)-4-amino-2-methylbutane-1-ol. The optical purity of (R)-4-amino-2-methylbutane-1-ol obtained above was 99.9% e.e. Filtration residue obtained by solid-liquid separation were combined, dissolved by heating in 200 g of water, 17 g of concentrated sulfuric acid was added thereto, the resulting mixture was cooled to 5° C. and subjected to solid-liquid separation. The amount of the recovered (R)-2-chloromandelic acid was 55 g.

EXAMPLE 13

In 150 g of water was dissolved, with heating, 100 g of a diastereomeric salt crystal having high optical purity obtained in the same manner as in Example 10, 30 g of a 48% aqueous sodium hydroxide solution was added thereto to decompose the salt, then the resulting reaction mixture was concentrated, 600 g of 2-butanol was added thereto while conducting concentration to replace most of the water with 2-butanol, and then the mixture was subjected to solid-liquid separation. The solution thus obtained was concentrated and then distilled in vacuo to obtain 30 g of (R)-4-amino-2-methylbutane-1-ol. The optical purity of (R)-4-amino-2-methylbutane-1-ol obtained was 99% e.e. Filtration residue obtained by solid-liquid separation was dissolved by heating in 200 g of water, 17 g of concentrated sulfuric acid was added thereto, the resulting mixture was cooled to 5° C. and subjected to solid-liquid separation. The amount of the recovered (R)-2-chloromandelic acid was 57 g.

EXAMPLE 14

In exactly the same manner as in Example 1 except for changing the solvent and the optically active organic acid used respectively to ethanol and (–)-dibenzoyl-L-tartaric acid, changing the seed crystal to a salt of (–)-dibenzoyl-L-tartaric acid with (R)-4-amino-2-methylbutane-1-ol and conducting no recrystallization, 0.58 g of diastereomeric salt crystal was obtained. The optical purity of optically active 4-amino-2-methylbutane-1-ol in the crystal was (R)-isomer 11.8% e.e.

EXAMPLE 15

In exactly the same manner as in Example 1 except for changing the optically active organic acid used to (+)-10- camphorsulfonic acid and the seed crystal to a salt of (+)-10-camphorsulfonic acid with (R)-4-amino-2-methylbutane-1-ol and conducting no recrystallization, 0.12 g of diastereomeric salt crystal was obtained. The optical purity of optically active 4-amino-2-methylbutane-1-ol in the crystal was (R)-isomer 2.98% e.e.

EXAMPLE 16

In exactly the same manner as in Example 1 except for changing the optically active organic acid used to (S)-(-)-3-phenyllactic acid, changing the seed crystal to a salt of (S)-(-)-3-phenyllactic acid with (R)-4-amino-2-methylbutane-1-ol and conducting no recrystallization, 0.87 g of diastereomeric salt crystal was obtained. The optical purity of optically active 4-amino-2-methylbutane-1-ol in the crystal was (R)-isomer 14.9% e.e.

EXAMPLE 17

In exactly the same manner as in Example 1 except for changing the optically active organic acid to (R)-mandelic acid, changing the seed crystal to a salt of (R)-mandelic acid with (R)-4-amino-2-methylbutane-1-ol and conducting no recrystallization, 0.58 g of diastereomeric salt crystal was obtained. The optical purity of optically active 4-amino-2-methylbutane-1-ol in the crystal was (R)-isomer 87.8%. e.e.

EXAMPLE 18

In exactly the same manner as in Example 1 except for changing the optically active organic acid used to N-acetyl-(D)-valine, changing the seed crystal to a salt of N-acetyl-(D)-valine with (R)-4-amino-2-methylbutane-1-ol and conducting no recrystallization, 0.34 g of diastereomeric salt crystal was obtained. The optical purity of optically active 4-amino-2-methylbutane-1-ol in the crystal was (R)-isomer 4.49% e.e.

Industrial Applicability

According to this invention, optically active 4-amino-2-methylbutane-1-ol useful as an intermediate for synthesizing optically active medicines and pesticides can be provided on an industrial scale in high yield, in high purity and at low cost. According to this invention, further, the reagent for optical resolution used can be recovered in high yield.

What is claimed is:

1. A process for producing optically active 4-amino-2-methylbutane-1-ol which comprises: treating racemic 4-amino-2-methylbutane-1-ol with an optically active organic acid to obtain a diastereomeric salt, crystallizing out the resulting diastereomeric salt, and subjecting the salt to solid-liquid separation, wherein said optically active acid is (i) dibenzoyl tartaric acid, (ii) 10-camphosulfonic acid, (iii) 3-phenyllatic acid, (iv) N-acetyl-(D)-valine, (v) an optically active mandelic acid derivative represented by the following formula (3),

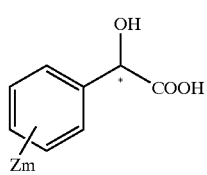

(3)

wherein Z is hydrogen or a straight or branched chain alkyl group having 1–10 carbon atoms, halogen atom, alkoxy group, hydroxyl group, nitro group, methylthio group or benzoyl group; * denotes asymmetric carbon; m is an integer of from 1 to 5; and, when m≧2, Z may be same as or different from each other.

2. A salt of optically active 4-amino-2-methylbutane-1-ol with an optically active organic acid, wherein the optically active organic acid is (i) an optically active mandelic acid derivative and the structure of the salt is represented by the formula (6)

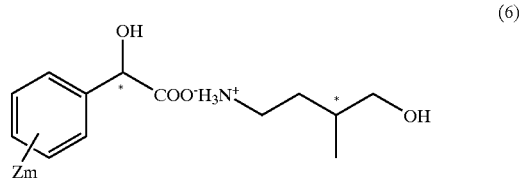

(6)

wherein Z denotes hydrogen or a straight or branched chain alkyl group having 1–10 carbon atoms, halogen atom, alkoxy group, hydroxyl group, nitro group, methylthio group or benzoyl group; * denotes asymmetric carbon; m is an integer of from 1 to 5; and, when m≧2, Z may be same as or different from each other, (ii) dibenzoyl tartaric acid, (iii) 10-camphosulfonic acid, (iv)3-phenyllatic acid, or (v) N-acetyl-(D)-valine.

3. A process for producing a salt of optically active 4-amino-2-methylbutane-1-ol with an optically active organic acid which comprises:
treating racemic 4-amino-2-methylbutane-1-ol with an optically active organic acid to obtain a diastereomeric salt, crystallizing out the resulting diastereomeric salt, and subjecting the salt to solid-liquid separation, wherein the optically active organic acid is (i) dibenzoyl tartaric acid, (ii) 10-camphosulfonic acid, (iii) 3-phenyllatic acid, (iv) N-acetyl-(D)-valine or (v) is an optically active mandelic acid derivative represented by the following formula (3) and the structure of the salt obtained is represented by the formula (6),

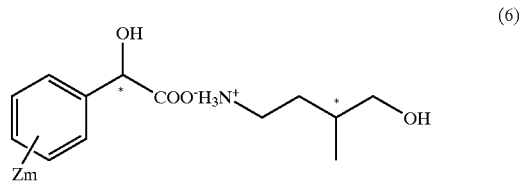

(6)

wherein Z is hydrogen or a straight or branched chain alkyl group having 1–10 carbon atoms, halogen atom alkoxy group, hydroxyl group, nitro group, methylthio group or benzoyl group; * denotes asymmetric carbon; m is an integer of from 1 to 5; and, when m≧2, Z may be same as or different from each other,

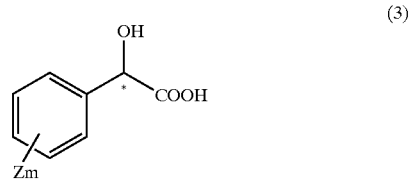

(3)

wherein Z and m are the same as in the formula (3).

4. A process for producing optically active 4-amino-2-methylbutane-1-ol which comprises:

bringing a diastereomeric salt of optically active 4-amino-2-methylbutane-1-ol and an optically active reagent for optical resolution into contact with a solvent and an alkali to decompose the salt, subjecting the resulting reaction mixture to solid-liquid separation to obtain a filtrate, and obtaining optically active 4-amino-2-methylbutane-1-ol from the filtrate, wherein the optically active reagent is (i) an optically active mandelic acid derivative wherein the diastereomeric salt thereof is represented by formula (6)

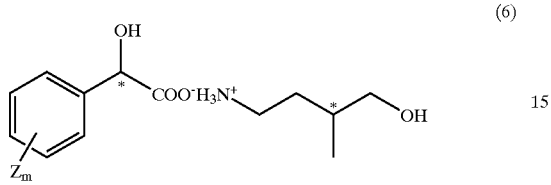

(6)

wherein Z denotes hydrogen or a straight or branched chain alkyl group having 1–10 carbon atoms, halogen atom, alkoxy group, hydroxyl group, nitro group, methylthio group or benzoyl group; * denotes asymmetric carbon; m is an integer of from 1 to 5; and, when m≧2, Z may be same as or different from each other, (ii) dibenzoyl tartaric acid; (iii) 10-camphosulfonic acid, (iv) 3-phenyllactic acid, or (v) N-acetyl-(D)-valine.

5. A process for recovering an optically active reagent for optical resolution used in producing optically active 4-amino-2-methylbutane-1-ol which comprises:

bringing a diastereomeric salt of optically active 4-amino-2-methylbutane-1-ol and an optically active optically resolving agent into contact with a solvent and an alkali to decompose the salt, subjecting the resulting reaction mixture to solid-liquid separation to obtain a filtration residue containing an alkali salt of the optically active reagent for optical resolution, bringing the filtration residue into contact with a solvent and an acid to crystallize out an optically active reagent for optical resolution, and subjecting the optically active reagent for optical resolution thus crystallized out to solid-liquid separation to recover it, wherein the optically active optically resolving agent is (i) dibenzoyl tartaric acid, (ii) 10-camphosulfonic acid, (iii) 3-phenyllatic acid, (iv) N-acetyl-(D)-valine or (v) an optically active mandelic acid derivative represented by the following formula (3).

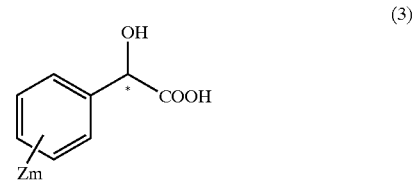

(3)

wherein Z is hydrogen or a straight or branched chain alkyl group having 1–10 carbon atoms, halogen atom, alkoxy group, hydroxyl group, nitro group, methylthio group or benzoyl group; * denotes asymmetric carbon; m is an integer of from 1 to 5; and, when m≧2, Z may be same as or different from each other.

* * * * *